US006416962B1

(12) United States Patent
Das et al.

(10) Patent No.: US 6,416,962 B1
(45) Date of Patent: *Jul. 9, 2002

(54) METHOD AND DEVICE FOR IDENTIFYING A MYCOBACTERIUM SPECIES RESPONSIBLE FOR A MYCOBACTERIAL INFECTION

(75) Inventors: Pranab Khumar Das, Castricum; Remco Maria Van Es, Koog aan de Zaan; Hendrik Jan Houthoff, Amsterdam, all of (NL)

(73) Assignee: Kreatech Biotechnology B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/166,663

(22) Filed: Oct. 5, 1998

Related U.S. Application Data

(63) Continuation-in-part of application No. 08/454,122, filed on Nov. 20, 1995, now Pat. No. 5,817,473.

(51) Int. Cl.$^7$ .................... G01N 33/554; A61K 39/40; A61K 39/04
(52) U.S. Cl. ................ 435/7.32; 424/150.1; 424/163.1; 424/168.1; 424/248.1; 435/4; 435/7.1; 435/174; 435/253.1
(58) Field of Search ........................... 435/4, 7.1, 7.32, 435/174, 253.1; 424/150.1, 168.1, 163.1, 248.1

(56) References Cited

U.S. PATENT DOCUMENTS

| 4,391,904 A | 7/1983 | Litman et al. ................. 435/7 |
| 5,817,473 A | * 10/1998 | Das et al. ................... 435/7.32 |

FOREIGN PATENT DOCUMENTS

| WO | WO 94/14069 | 6/1994 | ......... G01N/33/359 |

OTHER PUBLICATIONS

Vega–Lopez et al, Recognition of mycobacterial antigens by sera from patients with leprosy. Journal of Clinical Microbiology, vol. 26, No. 12, pp. 2472–2479, Dec. 1988.*

Sada, Eduardo D., et al., "An ELISA for the Serodiagnosis of Tuberculosis Using a 30,000–Da Native Antigen of *Mycobacterium tuberculosis*", *The Journal of Infectious Diseases*, 1990; 162:928–931.

Rambukkana, A., et al., "Subcellular Distribution of Monoclonal Antibody Defined Epitopes on Immunodominant *Mycobacterium tuberculosis* Proteins in the 30–kDA Region: Identification and Localization of 29/33–kDA Doublet Proteins on Mycobacterial Cell Wall", *Scand. J. Immunol.* 1991; 33, 763–775.

Vega–Lopez, Francisco, et al., "Recognition of Mycobacterial Antigens by Sera from Patients with Leprosy", *Journal of Clinical Microbiology*, Dec. 1988; 2474–2479.

Roche, Paul W., et al., "Antibody Responses to the 18–kDa Protein of Mycobacterium leprae in Leprosy and Tuberculosis Patients" *International Journal of Leprosy*, vol. 60, No. 2.

Havlir, Diane V., et al., Human Immune Response to *Mycobacterium tuberculosis* Antigens, *Infection and Immunity*, Feb. 1991; 665–670.

* cited by examiner

*Primary Examiner*—Rodney P Swartz
(74) *Attorney, Agent, or Firm*—Hoffmann & Baron, LLP

(57) ABSTRACT

The invention relates to a method for identifying a Mycobacterium species responsible for a mycobacterial infection in human or animal, comprising selecting a suitable mycobacterial species and strain; preparing at least one mycobacterial antigen, respectively antigen preparation; binding the antigen, respectively the antigen preparation to a suitable carrier; causing the binding antigen to react with antibodies from serum of an individual infected with a Mycobacterium species; making visible antigen-antibody reactions for a suitable antibody (sub-)class; and identifying the responsible Mycobacterium species on the basis of the reactions which are made visible. The invention further provides a diagnostic kit which takes the form of a dip-stick on which is arranged a carrier strip with mycobacterial antigens binding thereto, and means for visualizing antigen-antibody reactions occurring on the carrier after contact with the serum for testing. In another embodiment the diagnostic kit comprises a microtiter plate, in the wells of which a specified antibody is arranged, and means for making visible antigen-antibody reactions occurring in the wells after contact with the serum for testing. The third embodiment is an immunoblot with mycobacterial antigens separated by electrophoresis binding thereto, and means for visualizing antigen-antibody reactions occurring on the immunoblot after contact with the serum for testing.

53 Claims, 4 Drawing Sheets

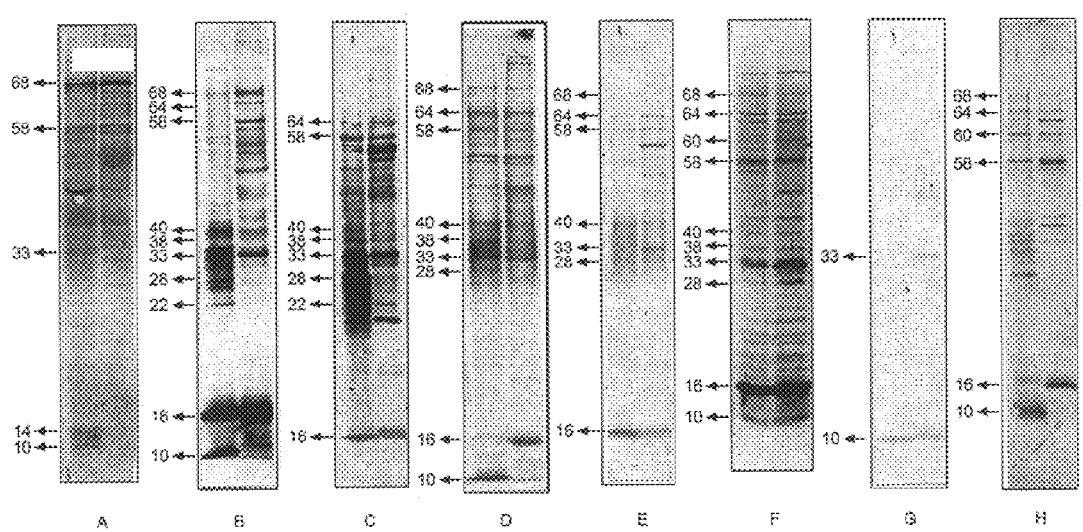

METHOD AND DEVICE FOR IDENTIFYING A MYCOBACTERIUM SPECIES RESPONSIBLE FOR A MYCOBACTERIAL INFECTION

CROSS REFERENCE TO RELATED APPLICATIONS

This application is a continuation-in-part of U.S. application Ser. No. 08/454,122 filed on Nov. 20, 1995, now U.S. Pat. No. 5,817,473 issued on Oct. 6, 1998, the entire disclosure of which is incorporated herein by reference. The priority application of the above parent application is Netherlands application No. 9202197, filed on Dec. 17, 1992 and published as PCT publication No. WO94/14069.

BACKGROUND OF THE INVENTION

1. Field of the Invention

The invention relates to a method for identifying a Mycobacterium species responsible for a mycobacterial infection in human or animal. The invention further relates to diagnostic kits for use in the method.

2. Description of the Related Art

The genus Mycobacterium which contains about 50 species, is responsible for a number of human and animal diseases which are known collectively as the mycobacterioses. The best known of these in humans are leprosy, caused by *M. leprae,* which affects more than ten million people worldwide, and tuberculosis, usually caused by *M. tuberculosis,* at least ten million new cases of which occur each year. Most other mycobacteria normally occur only as environmental saprophytes but can also cause opportunist diseases. This happens usually, but not only, in the case of people who have problems with their immune system, such as AIDS patients and people undergoing immunosuppression. These opportunist types comprise the slow-growing species *M. avium,* and the closely related *M. intracellulare* and *M. scrofulaceum* (often referred to together as MAIS complex), *M. kansasi, M. marinum* and *M. ulcerans,* and the fast-growing species *M. chelonae* and *M. fortuitum.* Although once rare, the incidence of opportunist mycobacterial diseases and tuberculosis shows a parallel increase in the western world with the incidence of AIDS. In addition there is limited but increasing evidence that mycobacteria or antigens thereof play a direct or indirect part in the etiology of a plurality of other diseases such as sarcoidosis and Crohn's disease and different auto-immune diseases such as auto-immune dermatitis, rheumatoid arthritis and diabetes. This could be attributed to a structural mimicry between epitopes of mycobacteria and those of the host.

The cell walls of mycobacteria are very complex and contain many lipids, some with structures unique to the genus. These structures comprise mycolinic acids and esters, peptido-glycolipde, arabino-galactane and lipo-arabinomanane. The lipid-rich mycobacterial cell walls are responsible for the characterizing coloring properties of the mycobacteria. They also enable mycobacteria to counter an attack by the immune system of the host. A number of species, once taken up into macrophages, are capable of surrounding themselves with a thick layer of secreted lipids.

Many different components of the mycobacteria begin an interaction with the immune system. These components comprise protein and hydrocarbon antigens, which can either be actively secreted by the mycobacteria or can form part of the cell wall or cell membrane. In addition they may be present in the cytoplasm, for instance in the cytoplasmic matrix, ribosomes and enzymes. Mycobacteria also possess immuno-modulating components such as immunosuppressing compounds and adjuvants. Consequently, a single mycobacterial species can induce a large variety of immune responses in different forms and with diverse specificities. It is therefore difficult to distinguish immune responses against species-specific components from cross reactions. For this reason it has therefore been found difficult to derive protein antigens suitable for the detection of species-specific humoral responses as a basis for a very sensitive and specific sero-diagnostic test for tuberculosis. Because the mycobacteria occur a great deal in the environment, human serum nearly always contains anti-mycobacterial antibodies.

In view of the problems with the specificity of protein antigens, a number of researchers, including the present inventors, have focused their attention on species-specific glycolipid antigens for the detection of specific humoral immune responses. Although the immune reactivity against mycobacteria is of the cell-mediated type and the humoral immune responses probably play a minor part in the total effector mechanism of mycobacterial immunity and immunopathology, studies in the antibody response to immuno-dominant mycobacterial cross-reactive antigen components (referred to hereinafter as "Im-CRAC") could shed light on the varying capability of the host to recognize different mycobacterial antigens. They could therefore provide indirect information relating to the nature of the immune recognition of, and response to, a specific mycobacterial pathogen.

SUMMARY OF THE INVENTION

It has now been found that the clinical manifestation of mycobacterial diseases appears to be related to the varying capability of an individual host to produce a humoral response to different mycobacterial immuno-cross-reactive antigen components (Im-CRAC). Each mycobacterial infection generates its own specific antibody response to a number of specified antigens. Analysis of the antibody-response by means of immunoblotting has demonstrated that the immuno-dominant Im-CRAC vary in accordance with the immunopathological manifestation of the mycobacterial diseases. It has been found that the sera of individuals which are infected with different Mycobacterium species cause different and distinguishing band patterns on immunoblots of mycobacterial antigens.

This discovery forms the basis of the present invention, whereby a method is provided for identifying a Mycobacterium species responsible for a mycobacterial infection in human or animal, comprising the steps of:

(a) selecting a suitable mycobacterial species and strain;

(b) preparing an antigen preparation comprising at least one mycobacterial antigen;

(c) binding the antigen, respectively the antigen preparation to a suitable carrier;

(d) causing the binding antigen to react with antibodies from serum of an individual infected with a Mycobacterium species;

(e) making visible antigen-antibody reactions for a suitable antibody (sub-)class; and (f) identifying the responsible Mycobacterium species on the basis of the reactions which are made visible.

In preference, the antigen preparation is separated by electrophoresis prior to step (c) and the carrier is a membrane to which the antigen is bound by means of electroblotting. This process is called Western blotting.

The invention also provides a method for identifying a Mycobacterium species responsible for a mycobacterial infection in a patient by testing a sample comprising antibodies from the patient, the method includes the steps of:

(a) providing an antigenic preparation of a Mycobacterium species, wherein the antigen preparation comprises two or more immuno-cross-reactive antigen components (ImCRACs); wherein the ImCRACs are bound to a solid carrier to form carrier-bound ImCRACs;

(b) contacting the carrier-bound ImCRACs with the sample under conditions suitable for antibody-antigen binding, to provide a set of carrier-bound antibody-ImCRACs; and (c) detecting the set of carrier-bound antibody-ImCRACs; the set of carrier-bound antibody-ImCRACs being characteristic of the Aycobacterium species.

The invention further provides a method for detecting or identifying an antibody reactive with a Mycobacterium species in a sample. The method includes the steps of:

(a) providing a solid phase carrier having bound thereto an antigen preparation from a culture of the Mycobacterium species, wherein the antigen preparation comprises two or more immuno-cross-reactive antigen components (ImCRACs), forming carrier-bound ImCRACs;

(b) contacting the carrier-bound ImCRACs with the sample under conditions suitable for binding of antibodies in the sample to the carrier-bound ImCRACs to provide a set of carrier-bound antibody-ImCRACs; and (c) detecting the set of carrier-bound antibody-ImCRACs; wherein the binding of the carrier-bound ImCRACs to antibodies of the sample exhibits a set of antibody-ImCRACs characteristic of the Mycobacterium species.

The invention yet further provides a diagnostic kit for the identification of antibodies elicited by a Mycobacterium species. The kit includes: (i) an antigenic preparation of a Mycobacterium species, wherein the antigen preparation comprises two or more immuno-cross-reactive antigen components (ImCRACs). The ImCRACs are bound to a solid carrier; and binding of the carrier-bound ImCRACs to antibodies reactive with the ImCRACs exhibits a set of antibody-ImCRACs characteristic of particular Mycobacterium species; and (ii) an antibody-enzyme conjugate directed against at least one antibody of an isotype selected from the group consisting of IgG, IgM and IgA.

BRIEF DESCRIPTION OF THE DRAWINGS

FIG. 2a shows an example of different Western blotting patterns developed after incubation with representative variable sera of tuberculous patients.

DETAILED DESCRIPTION OF THE PREFERRED EMBODIMENTS

Figure 1:
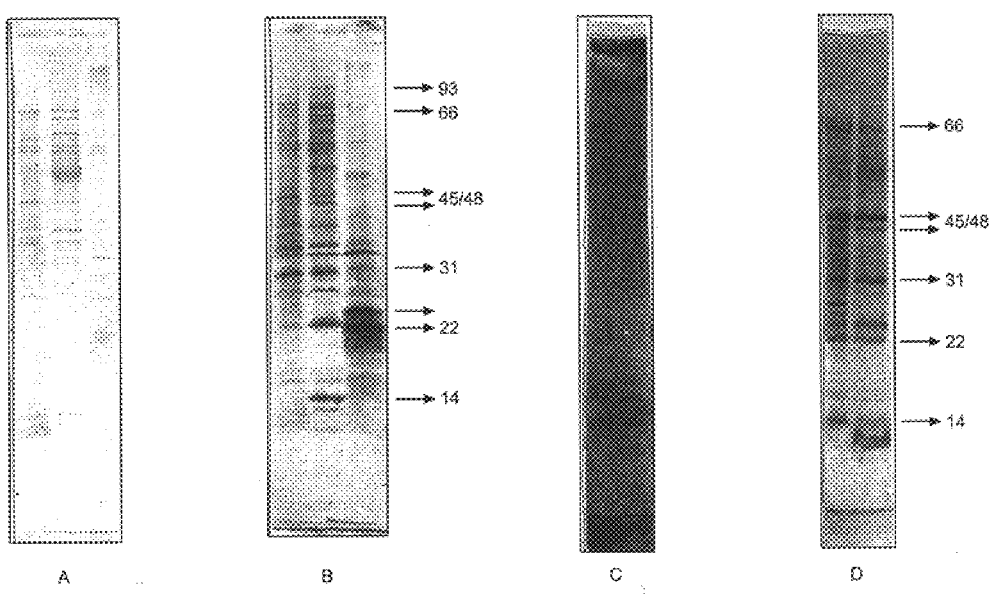
FIG. 1 shows an example of Western blotting patterns which are developed after incubation respectively with representative negative and positive sera (positive for bovine tuberculosis).

The Im-CRAC comprise namely a number of antigens with specific molecular weights which, as has now been found, after immunoblotting, exhibit a binding pattern which correlates to the disease or infection. The specific band pattern is characterized by the presence or absence of four individual components, for instance:

a region comprising different pronounced bands and/or overlapping bands, which can be observed as a smear ("region");

sharp single bands which are strongly positive ("band");

sharp double bands which are strongly positive ("doublet"); and other positive bands ("extra bands").

For a survey of the different antigens, their molecular weights and binding characteristics, see Table 1.

TABLE 1

Survey of characteristic bind patterns of mycobacterial Immuno-Cross-reactive Antigen Components.

| Antigen | Diagnostic for | MW range (in KDa) | Binding characteristic |
|---|---|---|---|
| A | J | <8 | band |
| B | T, B, J, | 10–16 | band |
| C | B, J, T, | 20–28 | band or region |
| D | L | 29/33 | doublet |
| E | B, J, T, | 31–40 | band or region |
| F | T | 38–40 | band or region |
| G | C, B, J, | 45/48 | doublet |
| H | T | 58–60 | band or region |
| I | L | 64/65 | doublet |
| J | J | 66 | band |
| K | T | 68 | band |
| L | L | 30–64 | region |

T: Human Tuberculosis
L: Leprosy
C: Crohn's Disease
B: Bovine Tuberculosis
J: Johne's Disease Each of the mycobacterioses is characterized by a specific banding pattern which is formed when a blot having thereon an antigen preparation of mycobacteria separated to size is incubated with serum of an infected individual.

Tables 2a–2f below show a survey of the banding patterns of a number of mycobacterial and immunological diseases.

TABLE 2a

Bovine tuberculosis
Regions (MW in KDa)

| Pattern | and/or 10–16 | and/or 20–28 | and/or 31–40 | and 45–48 |
|---|---|---|---|---|
| 1. | 14 KDa band | 22 KDa band 20–28 KDa region | 31 KDa band | 45/48 KDa doublet |

TABLE 2b

Johne's Disease
Regions (MW in KDa)

| Pattern | and/or >8 | and 10–16 | and/or 20–28 | and/or 31–40 | and 45–48 | and 66 |
|---|---|---|---|---|---|---|
| 1. | region | 14 KDa band | and 22 (25) - KDa band, and/or 27 KDa band | 31 KDa band | 45/48 KDa doublet | 66 KDa band |

TABLE 2c

Human Tuberculosis
Regions (MW in KDa)

| Pattern | 10–16 | 20–28 | 31–38 | 38–40 | 58–60 | 68 | other* |
|---|---|---|---|---|---|---|---|
| 1. | 10 and 16 KDa bands | / | 33 KDa band | region | band | / | +/– |
| 2. | 16 KDa single band | region | 33 KDa band | bands | region | / | +/– |
| 3. | 10 or 16 KDa band | / | / | bands | bands | / | +/– |
| 4. | 16 KDa band | / | 33 KDa band | region | bands | / | +/– |
| 5. | 10 and/or 16 KDa band | region | 33 KDa band | bands | bands and/or region | 68 KDa band | +/– |

*Extra bands and/or regions can color but are not diagnostic for Human Tuberculosis TABLE 2d Leprosy
Regions (MW in KDa)

| Pattern | 29–33 | 30–65 | 64–65 | other* |
|---|---|---|---|---|
| LL pattern 1 | 29/33 KDa doublet | / | / | +/– |
| TT pattern 1 | / | regions and/or bands | / | +/– |
| TT pattern 2 | / | regions and/or bands | 64/65 KDa doublet | +/– |
| TT pattern 3 | / | / | 64/65 KDa doublet | +/– |

TABLE 2e

Crohn's Disease
Regions (MW in KDa)

| Pattern | 45–48 | other* |
|---|---|---|
| 1. | 45/48 KDa doublet | +/– |

TABLE 2f

Rheumatoid Arthritis
Regions (MW in KDa)

| Pattern | and 42 KDa | and/or 80–90 KDa | and/or 58–60 KDa | and/or 14–18 KDa |
|---|---|---|---|---|
| 1. | band | region | region | region |

The method of the invention, such as an immunoblot, can be used to answer two questions. First, the presence of any positive band pattern will answer the question of whether a mycobacterial infection is present. Second, the presence of specific banding patterns indicates which mycobacterial species has caused the infection, and therefore what the nature and etiology of the disease will be.

The invention further relates to a heterogeneous enzyme immunoassay. The antigens for a heterogeneous enzyme immunoassay is preferably chosen from the group which consists of mycobacterial immuno-cross-reactive antigen components with a molecular weight of 29/33 KDa, 45/48 KDa, 64/65 KDa and a fraction designated with the term KP-100. These ImCRAC can be used separately or in combination with each other for serological diagnosis of the correlating diseases in a heterogeneous enzyme immunoassay (EIA).

In this form of assay, antibody-conjugates labeled with a standard enzyme are used. An important detail is that the enzyme activity does not change during the immunological reaction.

To test the immune response in patients to the selected antigens, use is made for instance of micro titer plates ("Solid Phase"). By means of standard published techniques the antigens are irreversibly immobilized on the surface of the wells in such a microtiter plate.

This binding takes place while retaining specific antigen determinants on the used antigens. After incubation with serum, in the wells of the micro titer plate, antibodies present therein can specifically form a complex with the irreversibly bound antigens.

After removal of non-binding serum components, binding antibodies are detected using an anti-antibody antibody labeled with an enzyme.

Binding of the enzyme is only possible when specific antibodies have adhered to the immobilized antigens. Substrate conversion by the binding enzyme to a visually or photometrically observable signal is thereby directly related to the presence of specific antibodies in the tested serum.

The choice of specificity of the enzyme-bound anti-antibody antibody determines the type of reaction that takes place. For instance, it may be desirable in some cases to demonstrate the specifically binding immunoglobulins of the IgG type, while in other cases immunoglobulins of the IgA and/or IgM type are just demonstrated.

The combination of antigen and immunoglobulin type defines the specificity of the test.

The said methods, that is, the immunoblot and the EIA, can be used as mutual confirmation.

In addition, for the serological diagnosis based on the said antigens, use can be made of a test stick as solid phase.

A particularly advantageous embodiment of the invention relates to a test stick, the so-called "dip-stick", which is used as solid phase in the heterogeneous enzyme immunoassay.

The said mycobacterial antigens can be irreversibly bound to such a dip-stick.

The antigen is brought into reaction with antibody from serum for testing by dipping the dip-stick in a serum sample for testing. The formed antigen-antibody complex can be made visible by subsequently dipping the dip-stick in an anti-antibody antibody-enzyme conjugate solution.

With the binding enzyme a substrate can then be converted to a visually or photometrically observable signal.

In another embodiment, the invention is a diagnostic kit for:
  an immunoblot assay; comprising ImCRAC antigens separated by electrophoresis as described above, immobilized on a solid carrier, in addition to an associated suitable detection system.
  a heterogeneous enzyme immunological assay; comprising a microtiter plate, the wells of which are coated with above mentioned antigens or antigen preparations, in addition to an associated suitable detection system.
  a dip-stick assay; comprising test sticks coated with antigen or antigen preparations, in addition to an associated suitable detection system.

The present invention will be further elucidated with reference to a number of examples which are given herein by way of illustration and are not intended to limit the invention.

EXAMPLE 1

Immunoblot

1. Preparation of Crude Mycobacterial Mass ("Starting Material")

The mycobacteria were cultured in commercially available Sauton medium supplemented with 2 g $MgSO_4$, 8 g citric acid, 2 g $K_2HPO_4$, 16 g asparagine, 2 g ($Fe^+$) ammonium citrate, and 240 mL glycerol. The bacteria were cultured under standard conditions. The cells were harvested by filtration of the culture medium with a 12 μm filter. The cells were subsequently resuspended in 20 mL PBS (phosphate-buffered salt solution) (pH 7.4) and the harvested cells were autoclaved under a pressure of 15 psi for 20 minutes in order to deactivate and sterilize the bacteria. The thus obtained bacterial mass can be stored at –80° C.

To determine the quantity of starting material a 1/100 dilution of the harvested autoclaved suspension in PBS was made. The optical density thereof, measured at 420 nm ($O.D._{420}$) must be 0.1. If necessary the concentrated bacterial mass is supplemented with PBS (pH 7.4) until the correct O.D. is obtained. An $O.D._{420}$ of 0.1 indicates the presence of $7 \times 10^{11}$ bacteria per 30 mL, which is equivalent to 12 g wet weight of the bacterial mass.

For preparation of a crude mycobacterial extract, 5 g wet weight of the bacterial mass was washed three times with PBS (pH 7.4). Centrifuging was then carried out at 3000×g until the mass precipitated. The pellet was suspended in 50 mL PBS and stirred carefully to reduce formation of lumps to a minimum. To prevent lump formation, 0.05% Tween 80 was added. To avoid bacterial contamination 3 mg penicillin/streptomycin was added to this solution. This material was then diluted with PBS to a final concentration of 2 g wet weight/mL.

The bacterial mass was subsequently broken open using an automatic French-X-press or RIBI press (American Instruments Company, Trevenollab. Inc. Maryland). The buckets were pre-cooled overnight at –20° C. Before use the buckets were held in a mixture of ethanol and dry ice (–20° C.). After the buckets were filled with 1 g bacterial mass per bucket of 5 mL and cooled at –80° C. for 20 minutes, the buckets were placed in the French-X-press and twelve tons of pressure was applied by pushing the plunger of the press. The buckets were then removed and cooled again at –80° C. for 20 minutes. The buckets were inverted and treated for the second time under the same conditions as the first time with the exception of pressure being ten tons. The sequence of cooling and breaking was then repeated five times. The disrupted cells were eluted with a suitable volume of PBS and subsequently centrifuged at 4° C. at 300×g for 10 minutes in order to remove the unbroken bacteria with the sediment. The collected supernatant was then centrifuged at 4° C. and 145,000×g for 2 hours. The pellet was suspended in 0.1 M Tris-HCl (pH 7.2), 0.01 M EDTA which contained 20 mM $MgSO_4 \cdot 7H_2O$ in a concentration of about 1 g per 10 mL. 1 mg RNase and 1 mg DNase were added per 10 mL volume. Samples were then incubated overnight at 4° C. with careful stirring, followed by incubation for 1 hour at 37° C. The lysate was centrifuged at 300×g and 4° C. for 10 minutes in order to remove the last-remaining unbroken bacteria (this material is referred to hereinafter as "starting material").

2. Manufacture of Membrane for Assays

A 12% polyacrylamide analytical gel of 1.5 mm thickness was casted according to normal standard procedures. No comb was used in the stacking gel. Five milligrams (5 mg) of the starting material, KP-100, or SP-100 (see Example 2) were used for each gel. Forty microliters (40 μL) of this material was diluted with 1.2 μL PBS. 300 μL 5×loading mixture (0.3 g 250 mM Tris-HCl, 1.0 mL 10% SDS, 1.0 mL 10% dithioerythritol, 5 mg 0.05% bromophenol blue) was then added.

Incubation was carried out for 20 minutes at 65° C. 1.5 mL of total sample were subsequently applied to the gel and electrophoresis performed under the following conditions: 150 V for the run through the stacking gel for 30 minutes and 100 V through the running gel for 6 hours.

To prepare a Western blot the proteins present in the gel were transferred at 50 V for 3 hours to a nitrocellulose membrane. After completion of the transfer the membrane was colored with 0.2% amido black for 2 minutes to check the membrane for irregularities and air bubbles. The membrane was the decolorized in 0.05% Tween 80 in PBS with 1% BSA (bovine serum albumin). The membrane was then cut into strips and was ready for use.

3. Immunodetection

The strips were incubated with human serum diluted 1:200 with PBS containing 3% BSA for 1 hour at room temperature. The strips were subsequently washed three times (for 3 minutes at a time) in PBS. The strips were then incubated with a goat anti-human immunoglobulin-alkaline phosphatase conjugate in a dilution of 1 to 1000 in PBS with 3% BSA and 0.05% Tween 80. The strips were then washed again three times in PBS, as before. The color was developed with an NBT/BCIP (nitroblue tetrazolium/Bromo, Chloro Indolyl phosphate) color solution (1 mg per 10 mL) to which 10 μL $H_2O_2$ were added. The strips were incubated for a maximum of 2 hours in 1 mL of this solution per strip. The color reaction was stopped by transferring the strips to 0.1 M Tris-HCl (pH 8.3), 0.01 M EDTA. The obtained patterns are interpreted by comparison with a reference pattern.

The results are shown in FIGS. 1 and 2a–2c.

FIG. 1 shown in the blots A and B an example of Western blotting patterns which are developed after incubation respectively with representative negative and positive sera (positive for bovine tuberculosis).

Blots C and D are exemplary Western blotting patterns which are developed after incubation with a representative negative serum sample (Blot C) or positive serum sample (Blot D) (positive for Cattle Jones Disease).

Blots A and B: Lane 1: BCG (Bacillus Calmette-Guérin) crude extract, Lane 2: crude extract of an *M. tuberculosis* strain, Lane 3: *M. bovis* crude extract.

Blots C and D: Lane 1: BCG derived KP-100, Lane 2: RIVM 7114 derived KP-100. RIVH is the abbreviation from the Netherlands National Institute of Public Health and Environmental Protection (Rijksinstituut voor Volksgezondheid en Milieuhgiene, Bilthoren, the Netherlands).

Interpretation of banding patterns from left to right is as follows.

Only the specific characteristics are stated herein.

Blot A: only the background bands can be observed in blots incubated with negative serum.

Blot B: region in the 10–16 KDa region in lane 3, 22 KDa band in lane 2, 31 KDa bands in lane 1 and 2, 14 KDa band in lane 2.

Blot C: only background bands can be observed in blots incubated with negative serum.

Blot D: 45/48 KDa doublet in lane 1 and 2, 22 and 25 KDa band in lane 1 and 2, 66 KDa band in lane 1 and 2, 27 KDa band in lane 1.

FIG. 2a is an example of different Western blotting patterns developed after incubation with representative variable sera of tuberculosis patients. Noticeable is the combination of different patterns demonstrating the presence of different dominant bands, as shown in table 1. These band patterns function as "hallmarks" for TB patients as diagnosed serologically.

Applicable to all blots (from left to right): Lane 1=BCG crude extract, Lane 2=crude extract of an *M. tuberculosis* strain.

Interpretation of banding patterns is as follows. Different blots (originating from different PAGE gels) are herein compared with each other.

Blot A: Mycobacterium avium infected patient.

Blot B–F: Tuberculosis patients.

Blot G: non-endemic negative serum.

Blot H: endemic negative serum (known recent contact, blot developed 2 weeks after patient returned to Netherlands from endemic range).

Only "hallmarks" are mentioned.

Blot A: Mycobacterium avium infected patients, sera, band at 68 KDa in lane 1 and 2, range in 10–16 KDa in lane 1, band in the 58–60 KDa region in lane 2. Patient shows low IgA titer in P-90 ELISA).

Blot B: 38–40 KDa band in lane 1 and 2, 10–16 KDa band in lane 1 and 2, band in 58–60 KDa region in lane 2, smear in 22–28 KDa region in lane 1.

Blot C: 16 KDa band in lane 1 and 2, bands in 58–60* KDa region in lane 1 and 2, bands in 38–40 KDa region in lane 1 and 2, smear in 22–28 KDa region in lane 1, 33 KDa band in lane 1 and 2.

Blot D: 10 KDa band in 10–16 KDa region in lane 1, 16 KDa band in 10–16 KDa region in lane 2, 68 KDa band in lane 1 and 2, bands in 58–60* KDa region in lane 1 and 2.

Blot E: smear in 33–38 KDa region in lane 1 and 2, 16 KDa bands in lane 1 and 2, bands in 58–60* KDa region in lane 2.

Blot F: bands in 10–16, 22–28, 38–40, 58–60 regions and 68 KDa band in both lanes 1 and 2.

Blot G: non-endemic negative serum.

Blot H: endemic negative serum (known contact).

Figure 2B:
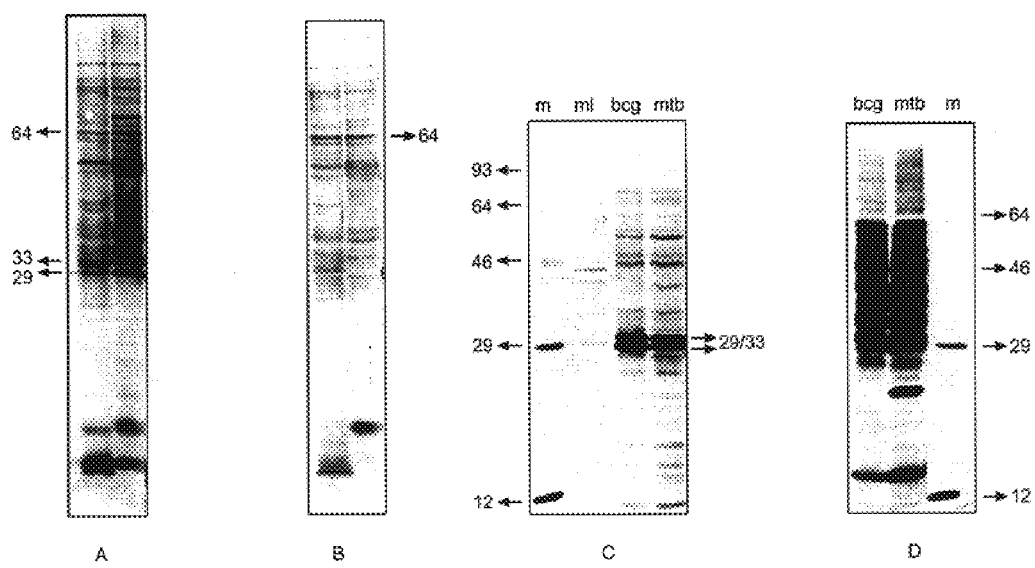
FIG. 2b shows an example of different Western blotting patterns developed after incubation with representative sera of patients with Lepromatous Leprosy (LL) and Tuberculous Leprosy (TT).

FIG. 2*b* is an example of different Western blotting patterns developed after incubation with representative sera of patients with Lepromatous Leprosy (LL), Blot A and C, and Tuberculous Leprosy (TT), Blot B and D.

The "hallmark" patterns are shown in table 1 and are for LL: distinctive 29/33 KDa doublet, and for TT: distinctive 64/65 KDa doublet (often observed as single band) or a very pronounced smear in the 30–64 KDa region.

To Blot A and B are applied: Lane 1: BCG crude extract, Lane 2: crude extract of a *M. tuberculosis* strain, Blot C: Lane 1: Molecular marker, Lane 2: not relevant, Lane 3: BCG crude extract, Lane 4: crude extract of an *M. tuberculosis* strain, Blot D: Lane 1: BCG crude extract, Lane 2: crude extract of an *M. tuberculosis* strain, Lane 3: Molecular marker.

Interpretation of banding patterns, wherein only the "hallmarks" are mentioned, is as follows:

Blot A/C: 29/33 KDa doublet in lane 1 and 2.

Blot B/D: 64/65 KDa doublet in lane 1 and 2.

The very intensive smear in the 30–64 KDa range on blot D is distinct.

Figure 2C:
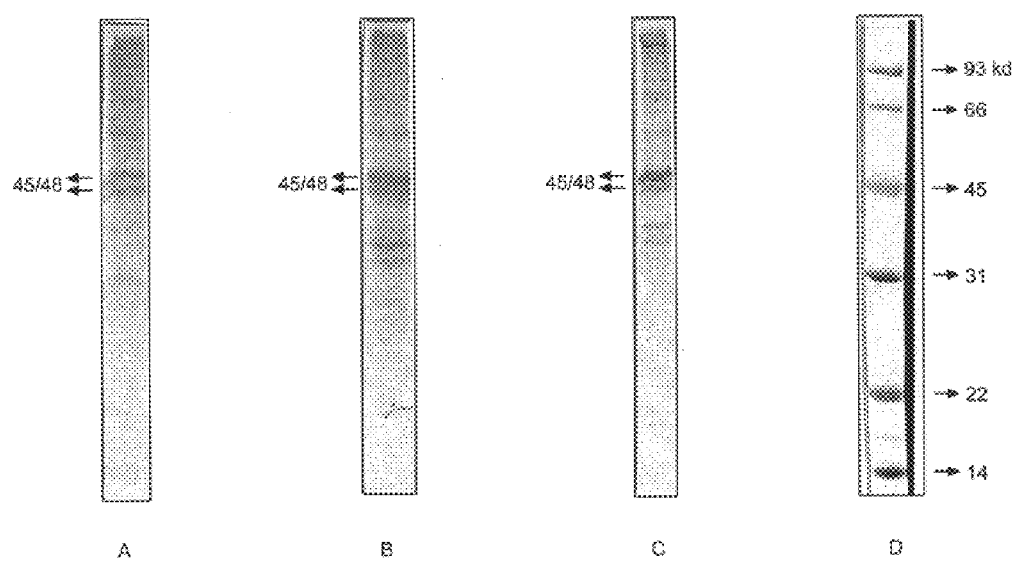
FIG. 2c shows an example of different Western blotting patterns developed after incubation with representative sera of patients with Crohn's Disease.

Finally, FIG. 2*c* is an example of different western blotting patterns developed after incubation with representative sera of patients with Crohn's Disease. The "hallmark" patterns are shown in table 3 and are for Crohn's Disease a pronounced 45/48 KDa doublet.

Applied to blot A is: BCG crude extract, blot B: crude extract of an *M. tuberculosis* stain, blot C: Mycobacterium avium crude extract, blot D: molecular marker.

Interpretation of banding patterns is as follows:

All lanes show a distinctive coloring of the 45/48 KDa doublet positively, which indicates Crohn's Disease. The 45/48 KDa doublet reacts positively in 65% of all Crohn patients.

EXAMPLE 2

Enzyme Immunoassay

1. Preparation of Antigens

The starting material prepared according to Example 1 was, depending on the chosen *M. tuberculosis* strain, centrifuged at 70,000×g to 120,000×g at 4° C. for 2 hours. The pellet was washed three times with PBS. Between the washing steps centrifuging took place at 70,000×g to 120,000×g at 4° C. for 2 hours. The pellet was collected and resuspended in 10 mL PBS. In addition to the supernatant in Example 1, SP-100 can also be used for immunoblots (Example 1) and enzyme immunoassays (this example). The suspension was subsequently sonicated for 2 minutes at 80 watts at 4° C. After the protein concentration was determined, quantities of 100 µL were frozen at a concentration of 1 mg/mL and stored at −80° C. until time of use (this preparation is designated with the term KP-100).

Thirty milligrams (30 mg) of the starting material was then applied in the presence of loading buffer onto a preparative 12% polyacrylamide gel of 0.5 cm thickness after 20 minutes of incubation at 65° C. Electrophoresis was carried out for 30 minutes at 150 V (stacking gel) and for 6 hours at 100 V (running or separating gel). The electrophoresis was stopped after the blue colorant band ("dry front") had ran off the gel. The gel was then cut into horizontal strips of 2 mm thickness which in turn were divided into pieces of 1 cm length. The gel pieces were each eluted overnight at 4° C. in a tube with 5 mL sterile distilled water. Thorough mixing thereafter took place and the remaining gel pieces were centrifuged to the bottom.

The elution was checked using a 12% polyacrylamide analytical gel of 1.5 mm thickness. The gel was cast with a comb. After 20 minutes incubation at 65° C., 40 µL of each tube with gel pieces was placed in the slots in the presence of 10 µL 5×loading mixture. The electrophoresis was carried out for 30 minutes at 150 V in the "stacking gel" and for 6 hours at 100 V in the "running or separating gel". The electrophoresis was stopped and the gel made ready for preparation of a Western blot according to the procedure described in Example 1. Similar results were obtained using HPLC, FPLC, and other routine separating procedures.

To establish which fractions contain the relevant antigens, strips of the blot were incubated with sera of patients with lepromatous leprosy, tuberculous leprosy and Crohn's Disease. Shown herewith are respectively the 29/33 KDa antigens, the 64/65 KDa antigen and the 45/48 KDa antigens. The complex formation was visualized using antihuman IgG peroxidase conjugate and DAB. The desired fractions were collected, combined and used to cast a microtiter plate (see below).

2. EIA

Microtiter plates are coated (via standard techniques) with either KP-100, SP-100, starting material, whole bacteria, 29/33 KDa, 64/65 KDa or 45/48 KDa antigens.

After coating, the plates are blocked with a 3% BSA solution in order to prevent a nonspecific binding of serum components. Plates are then dried and stored at 4° C.

2.1. Tuberculosis EIA Test (Microtiter Plates Coated with KP-100)

Test sera are pipetted in a 1:100 dilution into the coated wells of a microtiter plate. The reaction takes place for 1 hour at 37° C. Nonspecific serum components and non-binding serum components are washed away with a washing buffer. A second incubation with a suitable dilution of an anti-human IgA peroxidase conjugate is carried out again for 1 hour at 37° C., and excess conjugate is then washed away.

Detection of human antibodies of the sub-type IgA binding specifically to KP-100 takes place by adding TMB (tetramethylbenzidine) to the wells.

Binding enzyme results in the occurrence of a blue color which, after addition of a coloring stop solution, changes to yellow. This yellow color has an absorption maximum of 450 nm.

The intensity of the resulting color is proportional to the amount of bound KP-100-specific IgA.

The results are shown in the tables below.

In the described test patient and control sera are used from two different populations.
A=Endemic area (Africa, Ghana)
B=Non-endemic area (Europe, the Netherlands).

Each population is sub-divided into 4 sub-groups, namely:
Group 1=culture confirmed TB patients
Group 2=negative control group (normal healthy individuals)
Group 3=suspected positives (TB contacts)
Group 4=suspected negatives (no known data, but certainly no TB, possibly leprosy or other nonspecific mycobacteriosis)

The test is performed with two kits having different lot numbers and production dates.

Interpretation of the test results takes place on the basis of the so-called calibration line which is made up of control sera with a determined arbitrary unit definition which corresponds to a known OD value (1 unit, 4 units, and 8 units).

Each time a test is carried out the units are included in the assay. Found sample values can then be related to the unit definition.

A test serum can be considered positive when the result found in the test scores higher than 2.1 units.

A test serum can be considered negative when the result found scores lower than 1.2 units.

Test sera with unit values between 2.1 and 1.2 units fall into the set so-called reconfirmation zone. This means that in the first instance positivity or negativity for tuberculosis cannot be determined with this test.

Reconfirmation of these sera takes place using the described Western blot strips with which, after serum incubation on the basis of banding patterns and specific "hallmarks", an answer can be given to the question of whether the test serum is positive (bands present) or negative (bands absent).

TABLE 3

Population A. Endemic range:
Group 1:

| SERUM NO. | # UNITS | TEST SCORE | REMARKS |
|---|---|---|---|
| 1 | 2.44 | positive | culture positive |
| 2 | 3.43 | positive | culture positive |
| 3 | 1.78 | reconfirmation | culture positive |
| 4 | 1.37 | reconfirmation | culture positive |
| 5 | 5.74 | positive | culture positive |
| 6 | 3.21 | positive | culture positive |
| 7 | 1 66 | reconfirmation | culture positive |
| 8 | 2.00 | reconfirmation | culture positive |
| 9 | 2.00 | reconfirmation | culture positive |

TABLE 4

Population A. Group 2:

| SERUM NO. | # UNITS | TEST SCORE | REMARKS |
|---|---|---|---|
| 10 | 1.16 | negative | healthy individual |
| 11 | 0.86 | negative | healthy individual |
| 12 | 0.77 | negative | healthy individual |
| 13 | 0.64 | negative | healthy individual |
| 14 | 0.74 | negative | healthy individual |
| 15 | 0.79 | negative | healthy individual |

TABLE 5

Population A. Group 3:

| SERUM NO. | # UNITS | TEST SCORE | REMARKS |
|---|---|---|---|
| 16 | 3.13 | positive | sick individual |
| 17 | 1.57 | reconfirmation | sick individual |
| 18 | 1.59 | reconfirmation | sick individual |
| 19 | 5.39 | positive | sick individual |
| 20 | 1.97 | reconfirmation | sick individual |
| 21 | 2.29 | positive | sick individual |
| 22 | 0.48 | negative | sick individual |

TABLE 6

Population A. Group 4:

| SERUM NO. | # UNITS | TEST SCORE | REMARKS |
|---|---|---|---|
| 23 | 1.54 | reconfirmation | normal control |
| 24 | 1.76 | reconfirmation | normal control |
| 25 | 0.58 | negative | culture negative |
| 26 | 1.03 | negative | culture negative |
| 27 | 0.79 | negative | culture negative |
| 28 | 0.89 | negative | culture negative |

TABLE 7

Population B. Non-Endemic range:
Group 1:

| SERUM NO. | # UNITS | TEST SCORE | REMARKS |
|---|---|---|---|
| 1 | 2.24 | positive | culture positive |
| 2 | 2.53 | positive | culture positive |
| 3 | 4.40 | positive | culture positive |
| 4 | 14.95 | positive | culture positive |
| 5 | 16.82 | positive | culture positive |
| 6 | 10.54 | positive | culture positive |
| 7 | 5.70 | positive | culture positive |
| 8 | 6.72 | positive | culture positive |
| 9 | 5.06 | positive | culture positive |

TABLE 8

Population B.
Group 2:

| SERUM NO. | # UNITS | TEST SCORE | REMARKS |
|---|---|---|---|
| 10 | 1.04 | negative | healthy individual |
| 11 | 0.92 | negative | healthy individual |
| 12 | 0.85 | negative | healthy individual |
| 13 | 0.20 | negative | healthy individual |
| 14 | 0.42 | negative | healthy individual |
| 15 | 0.90 | negative | healthy individual |

TABLE 8-continued

Population B.
Group 2:

| SERUM NO. | # UNITS | TEST SCORE | REMARKS |
|---|---|---|---|
| 16 | 0.35 | negative | healthy individual |
| 17 | 0.73 | negative | healthy individual |

TABLE 9

Population B.
Group 3:

| SERUM NO. | # UNITS | TEST SCORE | REMARKS |
|---|---|---|---|
| 18 | 2.23 | positive | sick individual |
| 19 | 4.70 | positive | sick individual |
| 20 | 1.22 | reconfirmation | sick individual |
| 21 | 1.43 | reconfirmation | sick individual |
| 22 | 2.21 | positive | sick individual with TB history |
| 23 | 6.38 | positive | sick individual |
| 24 | 1.59 | reconfirmation | sick individual |

TABLE 10

Population B.
Group 4:

| SERUM NO. | # UNITS | TEST SCORE | REMARKS |
|---|---|---|---|
| 25 | 0.20 | negative | patient resistant to drug therapy |

What is claimed is:

1. A method for identifying a Mycobacterium species responsible for a mycobacterial infection in a patient by testing a sample comprising antibodies from the patient, the method comprising the steps of:
   (a) providing an antigenic preparation of a Mycobacterium species, wherein the antigen preparation comprises two or more immuno-cross-reactive antigen components (ImCRACs); wherein the ImCRACs are bound to a solid carrier to form carrier-bound ImCRACs;
   (b) contacting the carrier-bound ImCRACs with the sample under conditions suitable for antibody-antigen binding, to provide a set of carrier-bound antibody-ImCRACs; and
   (c) detecting the set of carrier-bound antibody-ImCRACs; wherein the set of carrier-bound antibody-ImCRACs is characteristic of the Mycobacterium species.

2. The method according to claim 1, wherein the sample comprising antibodies from the patient is a serum sample.

3. The method according to claim 1, wherein the set of the carrier-bound antibody-ImCRACs identifies the Mycobacterium species according to one of the following:
   a set of antibody-ImCRACs consisting of ImCRACs 10 Kda, 14 Kda, 16 Kda, 10–16 Kda, 22 Kda, 22–28 Kda, 29/33 Kda, 31 Kda, 33 Kda, 33–38 Kda, 38–40 Kda, 58–60 Kda, 68 Kda and 64/65 Kda identifies M. tuberulosis;
   a set of antibody-ImCRACs consisting of the ImCRAC 10–6 Kda identifies M. bovis,
   a set of antibody-ImCRACs consisting of ImCRACs 10–16 Kda, 58–60 Kda and 68 Kda identifies M. avium,
   a set of antibody-ImCRACs consisting of ImCRACs 29/33 Kda and 64/65 Kda identifies M. leprae,
   a set of antibody-ImCRACs consisting of ImCRACs 22 Kda, 25 Kda, 27 Kda, 29/33 Kda, 31 Kda, 45/48 Kda, 664/65 Kda and 66 Kda identifies Bacillus Calmette-Guerin, and
   a set of antibody-ImCRACs consisting of ImCRACs 22 Kda, 25 Kda, 45/48 Kda and 66 Kda identifies RIVM 7114.

4. The method according to claim 1, wherein the infection by the Mycobacterium species is associated with one or more of the following diseases: tuberculosis, Johne's disease, Crohn's disease, rheumatoid arthritis, tuberculous leprosy or lepromatous leprosy.

5. The method according to claim 1, wherein the antigen preparation of step (a) is separated by electrophoresis and the carrier is a membrane to which the ImCRACS are transferred by electroblotting.

6. The method according to claim 5, wherein the membrane is a nitrocellulose membrane.

7. The method according to claim 5, wherein the set of the carrier-bound antibody-ImCRACs comprise a band, a doublet, an extra band or a smear.

8. The method according to claim 1, wherein the antigen preparation of the Mycobacterium species is a total protein preparation.

9. The method according to claim 8, wherein the antigen preparation is a KP-100 fraction or an SP-100 fraction of the total protein preparation.

10. The method according to claim 1, wherein the solid carrier is a surface of a microtiter plate well.

11. The method according to claim 10, wherein each of the two or more ImCRACs of the antigen preparation are separated and each is bound to a surface of a separate well of the microtiter plate.

12. The method according to claim 11, wherein a step of: removing the antibodies that do not bind, is incorporated between steps (b) and (c).

13. The method according to claim 1, wherein the ImCRAC is characterized by molecular weight.

14. The method according to claim 13, wherein the set of the carrier-bound antibody-ImCRACs is a set comprising antibody-ImCRACs including an antigen having a molecular weight selected from the group consisting of 10–16 Kda, 14 Kda, 20–28 Kda, 27 Kda, 29/33 Kda (doublet), 31 Kda, 31–40 Kda, 38–40 Kda, 45/48 Kda (doublet), 58 60 Kda, 64/65 Kda (doublet), 66 Kda and 68 Kda.

15. The method according to claim 13, wherein the two or more sets of carrier-bound antibody-ImCRACs characteristic of particular Mycobacterium species comprise a Mycobacterium species selected from the group consisting of M. tuberculosis, M. bovis, M. avium, Bacillus Calmette-Guerin and RIVM 7114.

16. The method according to claim 1, wherein the carrier-bound antibody-ImCRACs are detected by using at least one antibody-enzyme conjugate directed against at least one antibody of an isotype selected from the group consisting of IgG, IgM and IgA.

17. The method according to claim 16, wherein the antibody-enzyme conjugate acts on a fluorogenic compound to produce a detectable fluorescent compound.

18. The method according to claim 16, wherein the carrier-bound antibody-ImCRACs are detected by an immunometric assay.

19. The method according to claim 16, wherein the antibody-enzyme conjugate acts on a chromogenic compound to produce a detectable colored compound.

20. The method according to claim 19, wherein the enzyme of the antibody-enzyme conjugate is selected from the group consisting of peroxidase, beta-galactosidase and alkaline phosphatase.

21. The method according to claim 16, wherein the solid carrier is a dip-stick.

22. The method according to claim 21, wherein the set of the carrier-bound antibody-ImCRACs detected on the dipstick is a set of ImCRACs comprising a band or doublet selected from the group consisting of the 10–16 Kda band, the 14 Kda band, the 20–28 Kda band, the 27 Kda band, the 29/33 Kda doublet, the 31 Kda band, the 31–40 Kda band, the 38–40 Kda band, the 45/48 Kda doublet, the 58–60 Kda band, the 64/65 Kda doublet, the 66 Kda band and the 68 Kda band.

23. The method according to claim 21, wherein the set of ImCRACs identifies the Mycobacterium species according to one of the following:
a set of ImCRACs consisting of ImCRACs 10 Kda, 14 Kda, 16 Kda, 10–16 Kda, 22 Kda, 22–28 Kda, 29/33 Kda, 31 Kda, 33 Kda, 33–38 Kda, 38–40 Kda, 58–60 Kda, 68 Kda and 64/65 Kda identifies *M. tuberulosis;*
a set of ImCRACs consisting of the ImCRAC 10–16 Kda identifies *M. bovis,*
a set of ImCRACs consisting of ImCRACs 10–16 Kda, 58–60 Kda and 68 Kda identifies *M. avium,*
a set of ImCRACs consisting of ImCRACs 29/33 Kda and 64/65 Kda identifies *M. leprae,*
a set of ImCRACs consisting of ImCRACs 22 Kda, 25 Kda, 27 Kda, 29/33 Kda, 31 Kda, 45/48 Kda, 664/65 Kda and 66 Kda identifies Bacillus Calmette-Guerin, and
a set of ImCRACs consisting of ImCRACs 22 Kda, 25 Kda, 45/48 Kda and 66 Kda identifies RIVM 7114.

24. A method for detecting or identifying an antibody reactive with a Mycobacterium species in a sample, comprising:
(a) providing a solid phase carrier having bound thereto an antigen preparation from a culture of the Mycobacterium species, wherein the antigen preparation comprises two or more immuno-cross-reactive antigen components (ImCRACs), forming carrier-bound ImCRACs;
(b) contacting the carrier-bound ImCRACs with the sample under conditions suitable for binding of antibodies in the sample to the carrier-bound ImCRACs to provide a set of carrier-bound antibody-ImCRACs; and
(c) detecting the set of carrier-bound antibody-ImCRACs;
wherein the binding of the carrier-bound ImCRACs to antibodies of the sample exhibits a set of antibody-ImCRACs characteristic of the Mycobacterium species.

25. The method according to claim 24, wherein the antigen preparation is separated by electrophoresis and the carrier is a membrane to which the ImCRACS are bound by electroblotting.

26. The method according to claim 24, wherein the membrane is a nitrocellulose membrane.

27. The method according to claim 24, wherein the antigen preparation of the Mycobacterium species is a total protein preparation.

28. The method according to claim 24, wherein the antigen preparation is a KP-100 or SP-100 fraction of the total protein preparation.

29. The method according to claim 24, wherein the set of the carrier-bound antibody-ImCRAC comprises an ImCRAC selected from the group consisting of: 10–16 Kda, 14 Kda, 20– 28 Kda, 27 Kda, 29/33 Kda, 31 Kda, 31–40 Kda, 38–40 Kda, 45/48 Kda, 58–60 Kda, 64/65 Kda, 66 Kda and 68 Kda.

30. The method according to claim 24, wherein the set of ImCRACs identifies the Mycobacterium species according to one of the following:
a set of ImCRACs consisting of ImCRACs 10 Kda, 14 Kda, 16 Kda, 10–16 Kda, 22 Kda, 22–28 Kda, 29/33 Kda, 31 Kda, 33 Kda, 33–38 Kda, 38–40 Kda, 58–60 Kda, 68 Kda and 64/65 Kda identifies *M. tuberulosis;*
a set of ImCRACs consisting of ImCRAC 10–16 Kda identifies *M. bovis,*
a set of ImCRACs consisting of ImCRACs 10–16 Kda, 58–60 Kda and 68 Kda identifies *M. avium,*
a set of ImCRACs consisting of ImCRACs 29/33 Kda and 64/65 Kda identifies *M. leprae,*
a set of ImCRACs consisting of ImCRACs 22 Kda, 25 Kda, 27 Kda, 29/33 Kda, 31 Kda, 45/48 Kda, 664/65 Kda and 66 Kda identifies Bacillus Calmette-Guerin, and
a set of ImCRACs consisting of ImCRACs 22 Kda, 25 Kda, 45/48 Kda and 66 Kda identifies RIVM 7114.

31. The method according to claim 24, wherein the library of two or more sets of carrier-bound Ab-ImCRAC complexes characteristic of particular Mycobacterium species comprises a Mycobacterium species selected from the group consisting of *M. tuberculosis, M. bovis, M. avium,* Bacillus Calmette-guerin and RIVM 7114.

32. The method according to claim 24, wherein the solid phase carrier is a surface of a well of a microtiter plate.

33. The method according to claim 32, wherein each of the two or more ImCRACs of the antigen preparation are separated and each is bound to a surface of a separate well of the microtiter plate.

34. The method according to claim 33, wherein a step of:
removing the antibodies that do not bind, is incorporated between steps (b) and (c).

35. The method according to claim 24, wherein the substrate-bound antibody-ImCRAC complexes are made visualizable by using at least one antibody-enzyme conjugate directed against at least one antibody of an isotype selected from the group consisting of IgG, IgM and IgA.

36. The method according to claim 35, wherein the antibody-enzyme conjugate acts on a chromogenic compound to produce a detectable colored compound.

37. The method according to claim 36, wherein the enzyme of the antibody-enzyme conjugate is selected from the group consisting of peroxidase, beta-galactosidase and alkaline phosphatase.

38. The method according to claim 35, wherein the antibody-enzyme conjugate acts on a fluorogenic compound to produce a detectable fluorescent compound.

39. The method according to claim 24, wherein the solid carrier is a dip-stick.

40. The method according to claim 39, wherein the set of the carrier-bound antibody-ImCRACs detected on the dipstick is an antibody-ImCRAC set comprising a band or doublet selected from the group consisting of the 10–16 Kda band, the 14 Kda band, the 20–28 Kda band, the 27 Kda band, the 29/33 Kda doublet, the 31 Kda band, the 31–40 Kda band, the 38–40 Kda band, the 45/48 Kda doublet, the 58–60 Kda band, the 64/65 Kda doublet, the 66 Kda band and the 68 Kda band.

41. The method according to claim 39, wherein the antibody-ImCRAC set identifies the Mycobacterium species according to one of the following:

a set of ImCRACs consisting of ImCRACs 10 Kda, 14 Kda, 16 Kda, 10–16 Kda, 22 Kda, 22–28 Kda, 29/33 Kda, 31 Kda, 33 Kda, 33–38 Kda, 38–40 Kda, 58–60 Kda, 68 Kda and 64/65 Kda identifies *M.tuberulosis;* a set of ImCRACs consisting of ImCRAC 10–16 Kda identifies *M. bovis,* a set of ImCRACs consisting of ImCRACs 10–16 Kda, 58–60 Kda and 68 Kda identifies *M. avium,* a set of ImCRACs consisting of ImCRACs 29/33 Kda and 64/65 Kda identifies *M. leprae,* a set of ImCRACs consisting of ImCRACs 22 Kda, 25 Kda, 27 Kda, 29/33 Kda, 31 Kda, 45/48 Kda, 664/65 Kda and 66 Kda identifies Bacillus Calmette-Guerin, and a set of ImCRACs consisting of ImCRACs 22 Kda, 25 Kda, 45/48 Kda and 66 Kda identifies RIVM 7114.

42. A diagnostic kit for the identification of antibodies elicited by a Mycobacterium species, comprising:

(i) an antigenic preparation of a Mycobacterium species, wherein the antigen preparation comprises two or more immuno-cross-reactive antigen components (ImCRACs); wherein the ImCRACs are bound to a solid carrier; and wherein binding of the carrier-bound ImCRACs to antibodies reactive with the ImCRACs exhibits a set of antibody-ImCRACs characteristic of particular Mycobacterium species; and (ii) an antibody-enzyme conjugate directed against at least one antibody of an isotype selected from the group consisting of IgG, IgM and IgA.

43. The diagnostic kit according to claim 42, wherein the solid carrier is a dip-stick, a microtiter well, a nitrocellulose membrane or a nylon membrane.

44. The diagnostic kit according to claim 42, further comprising a chromogenic substrate or a fluorogenic substrate suitable for detection of the antibody-enzyme conjugate.

45. The diagnostic kit according to claim 42, to identify *M. bovis* reactivity, wherein the ImCRACs comprise an ImCRAC with a molecular weight of 10–16 Kda.

46. The diagnostic kit according to claim 42, to identify *M. avium,* wherein the ImCRACs comprise ImCRACs with molecular weights 10–16 Kda, 58–60 Kda and 68 Kda.

47. The diagnostic kit according to claim 42, to identify *M. leprae.* wherein the ImCRACs comprise ImCRACs with molecular weights 29/33 Kda and 64/65 Kda.

48. The diagnostic kit according to claim 42, to identify Bacillus Calmette-Guerin, wherein the ImCRACs comprise ImCRACs with molecular weights 22 Kda, 25 Kda, 27 Kda, 29/33 Kda, 31 Kda, 45/48 Kda, 664/65 Kda and 66 Kda.

49. The diagnostic kit according to claim 42, to identify RIVM 7114, wherein the ImCRACs comprise ImCRACs with molecular weights 22 Kda, 25 Kda, 45/48 Kda and 66 Kda.

50. The diagnostic kit according to claim 42, wherein the ImCRACs comprise ImCRACs with molecular weights 10–16 Kda, 14 Kda, 20–28 Kda, 27 Kda, 29/33 Kda, 31 Kda, 31–40 Kda, 38–40 Kda, 45/48 Kda, 58–60 Kda, 64/65 Kda, 66 Kda and 68 Kda.

51. The diagnostic kit according to claim 42, wherein the enzyme of the antibody-enzyme conjugate is selected from the group consisting of peroxidase, beta-galactosidase and alkaline phosphatase.

52. The diagnostic kit according to claim 51, wherein the ImCRACs are characterized by molecular weight.

53. The diagnostic kit according to claim 52, wherein the ImCRACs comprise two or more antigens selected from the group consisting of ImCRACs of molecular weight 10 Kda, 14 Kda, 16 Kda, 10–16 Kda, 22 Kda, 22–28 Kda, 29/33 Kda, 31 Kda, 33 Kda, 33–38 Kda, 38–40 Kda, 58–60 Kda, 68 Kda and 64/65 Kda.

* * * * *

UNITED STATES PATENT AND TRADEMARK OFFICE
CERTIFICATE OF CORRECTION

PATENT NO.   : 6,416,962 B1
DATED        : September 5, 2002
INVENTOR(S)  : Das et al.

It is certified that error appears in the above-identified patent and that said Letters Patent is hereby corrected as shown below:

Column 13,
Lines 65, now reads "10-6 Kda identifies", was correctly presented in the substitute specification as -- 10-16 Kda identifies --;

Column 16,
Line 29, now reads "Calmette-guerin", was correctly presented in the substitute specification as -- Calmette-Guerin --; and Column 14,
Line 46, now reads "58 60 Kda", was correctly presented in the substitute specification as -- 58-60 Kda --.

Signed and Sealed this

Twenty-sixth Day of November, 2002

Attest:

Attesting Officer

JAMES E. ROGAN
Director of the United States Patent and Trademark Office